April 19, 1938. A. F. J. BAUR Plant Pat. 274
CARNATION
Filed July 3, 1937
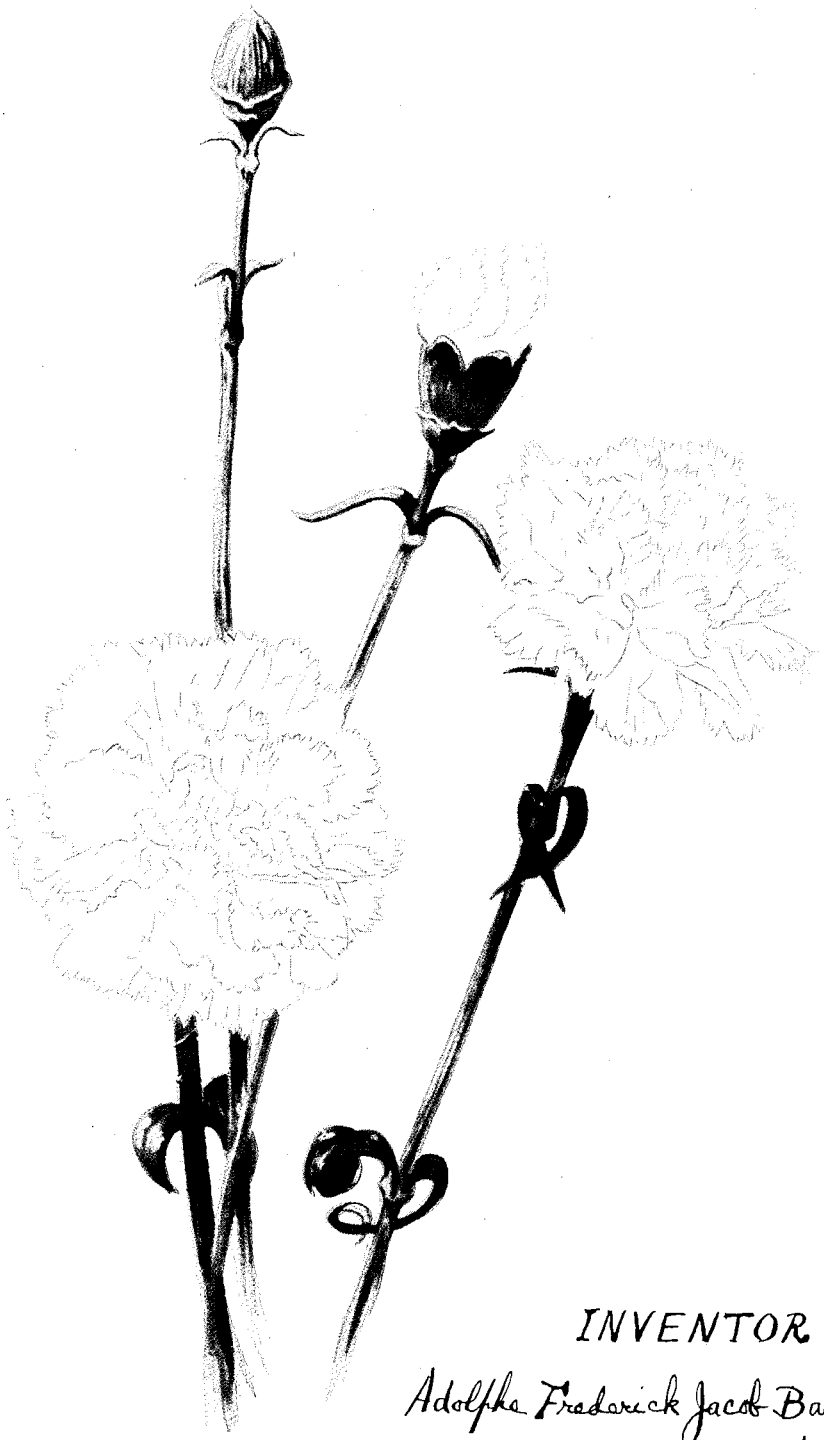
INVENTOR
Adolphe Frederick Jacob Baur
By Orville M. Kile
Plant Patent Agent Patented Apr. 19, 1938

Plant Pat. 274

UNITED STATES PATENT OFFICE

274

CARNATION

Adolphe Frederick Jacob Baur, Indianapolis, Ind., assignor to Baur-Steinkamp and Company, Incorporated, Indianapolis, Ind.

Application July 3, 1937, Serial No. 151,926

1 Claim. (Cl. 47—60)

My present invention relates to improvements in carnations usually known as greenhouse forcing carnations. The purpose of my invention is to provide a superior type of carnation in the novel cream or yellow class.

The present variety is a seedling and is the result of definite breeding efforts, being a cross between North Star and seedling #10,929, an undisseminated variety developed by me. This new variety has been asexually reproduced over a period of five years and its characteristics have persisted without change.

The accompanying illustration shows a front view and a side view of a fully opened flower, a tight bud, a partly opened bud, together with some stems and a few leaves. It indicates the characteristic features of this new variety but it must be understood that the artist cannot fully portray the color effects, there being a tendency to use deeper color tones in the shaded areas as a means of emphasizing the petal outlines. Color references indicate Ridgway's Color Standards and Nomenclature.

The known variety which most nearly resembles this new variety is its female parent, North Star. The principal differences between these two varieties are that the new variety is heavier and stronger in growth and produces larger and fuller blossoms having about twice as many petals as does the North Star.

Following is a more detailed description of this new variety.

*The plant*

*Growth habit.*—Upright and vigorous, attaining a height of 30 inches in midwinter.

*Foliage.*—Moderate in amount, leaves curling.

*Stems.*—Straight, usually strong although not exceptionally heavy. Color, Antique Green (Plate VI).

*The blossom*

*Size and shape.*—Medium size (larger than North Star). Full, folded center. Regular.

*Color.*—Barium Yellow (Plate XVI) with occasional flecks of pink and of white occurring on the blossom (one to three flecks to each bloom). The full, folded center gives a general color effect of a slightly darker shade—Citron Yellow (Plate XVI).

*Petalage.*—About 50 petals. Considerably folded and curled, especially in center of flower.

*Petals.*—Outer petals measure 2 inches in length. Irregularly serrated.

*Calyx.*—Continuous tube having five deep-cut lobes. One to one and one-fourth inches long. Never splits. Color is Absinthe Green to Light Cress Green (Plate XXXI).

*Bracts.*—Unusually large in proportion to length of calyx.

*Reproductive organs*

*Pistils:*—

*Ovary.*—Very large for size of flower—⅜ inch long. Many ovules.

*Stigmas.*—Three or four arise from top of ovary. White. One and one-fourth inches in length.

*Stamens.*—Small, stringy, white. Arise from base of ovary. Have small anthers.

Having thus disclosed my invention, what I claim as new is:

The variety of yellow carnation essentially as shown and described, characterized particularly by its exceptionally strong calyx, its heavier and stronger growth, and its larger blossoms with relatively large number of petals as compared with known yellow varieties.

ADOLPHE FREDERICK JACOB BAUR.